United States Patent [19]

Beltrop et al.

[11] Patent Number: 4,771,641

[45] Date of Patent: Sep. 20, 1988

[54] SAMPLE DIVIDER

[75] Inventors: Herbert Beltrop, Hamm; Helmut Kronemeyer, Oelde, both of Fed. Rep. of Germany

[73] Assignee: Krupp Polysius AG, Beckum, Fed. Rep. of Germany

[21] Appl. No.: 101,139

[22] Filed: Sep. 25, 1987

[30] Foreign Application Priority Data

Nov. 5, 1986 [DE] Fed. Rep. of Germany ....... 3637757

[51] Int. Cl.$^4$ .............................................. G01N 1/00
[52] U.S. Cl. ............................. 73/863.52; 73/863.31; 73/863.43; 73/863.61; 73/863.71
[58] Field of Search ........... 73/863.51, 863.52, 863.53, 73/863.54, 863.55, 863.56, 863.57, 863.58, 863.61, 863.41, 863.42, 863.43, 863.44, 863.45, 863.71, 863.31

[56] References Cited

U.S. PATENT DOCUMENTS

| 682,528 | 9/1901 | Calkins | 73/863.52 |
|---|---|---|---|
| 797,144 | 8/1905 | Nickerson | 73/863.52 |
| 1,160,036 | 11/1915 | Boerner | 73/863.51 |
| 2,405,486 | 8/1946 | Bauer | 73/863.51 |
| 2,848,144 | 8/1958 | Haskell et al. | 73/863.45 |
| 3,098,390 | 7/1963 | Bourne et al. | 73/863.51 |
| 4,126,043 | 11/1978 | Schurmann | 73/863.51 |
| 4,524,628 | 6/1985 | Knudtson et al. | 73/863.43 |
| 4,672,856 | 6/1987 | Marrs et al. | 73/863.52 |
| 4,718,288 | 1/1988 | Leschonski et al. | 73/863.52 |

Primary Examiner—Tom Noland
Assistant Examiner—Robert P. Bell
Attorney, Agent, or Firm—Learman & McCulloch

[57] ABSTRACT

A sample divider for fine-grained loose material samples contains - arranged symmetrically below one another - a sample delivery pipe, a divider and collecting vessels for sub-samples provided below the divider. The divider is constructed as a divider cone which has distributed over its base surface sample distribution holes to which a plurality of first sub-sample pipes is connected, below which are arranged a collecting funnel, a second divider cone and below that a plurality of second sub-sample pipes which are connected to the collecting vessels. In this way a starting sample quantity can be divided up into a comparatively large number of sub-sample quantities extremely well and reliably with the sample only passing through the sample divider once.

11 Claims, 3 Drawing Sheets

SAMPLE DIVIDER

The invention relates to a sample divider for fine-grained samples of loose material.

BACKGROUND OF THE INVENTION

In plants where loose material is processed it is often necessary to take samples of the loose material and in particular to study their composition. The loose material can in particular be mineral and chemical material as well as foodstuffs. In order to obtain representative samples of loose material for the relevant studies in a laboratory, the samples are taken from a resting quantity of loose material or from a flowing stream of loose material, and the sample quantity is generally too large and must then be divided up into representative sub-samples which are suitable for processing. It is for this purpose that the sample divider is used in practice.

One construction of a sample divider which is used very frequently in the art is the so-called riffle sample divider in which a sample of loose material to be divided up is delivered to a delivery funnel with a connecting pipe or connecting shaft arranged below it from which the starting sample is led to a divider which consists essentially of a row of rods arranged so that they are spaced from one another and form parallel slots and are inclined alternately towards two different sides, by means of which a starting sample should be evenly distributed to two sample collecting vessels. If a starting sample is to be divided into a larger number of sub-samples, then each of the sub-samples must be divided up again or a number of times, which is extremely laborious above all for large installations preparing samples in large laboratories.

A further construction is also known in the art in which a rotating pipe is arranged inside a symmetrical conical or biconical container, is driven by an appropriate drive means so that it rotates uniformly and connects an upper central sample delivery pipe successively to a plurality of sub-sample collecting vessels provided at the lower end of the container. In this known sample divider it is necessary for the rotating pipe to reliably retained and mounted and for a suitably arranged and continuously operating rotary drive arrangement to be provided.

SUMMARY OF THE INVENTION

The object of the invention is to provide a sample divider for this type application, in which rotating parts are avoided and a relatively simple construction facilitates reliable division of a sample of loose material into any number of sub-samples of any size.

By means of the construction and sensible arrangement of the essential components in the sample divider according to the invention a starting sample delivered via the sample delivery pipe is first of all evenly divided by the uppermost, first divider cone for the first time and led to the sample distribution holes which are distributed over the periphery of its base surface and from there to the first sub-sample pipes located underneath which are closed at their lower ends by their valves and thus each recieve one sub-sample. The number and size of these first sub-sample pipes are sufficient to enable them to receive one entire starting sample altogether. After the starting sample has been distributed evenly over the first sub-sample pipe all or only a selected number of the first sub-sample pipes can be opened via their valves so that these sub-samples, which can overall correspond to a desired and combinable sample quantity, are led together in a collecting funnel and from there are again divided via a discharge pipe, a second divider cone arranged centrally below it and second sub-sample pipes into sub-samples which are led directly into the appertaining collecting vessels.

In the tests on which the invention is based it was shown that using the sample divider according to the invention a starting sample of loose material can be divided extremely evenly into the desired sub-samples. This is partly due to the cooperation of a divider cone with the sliding sleeve, the lower opening end of which is movable in a pulsing fashion towards the surface of the appertaining divider cone to form a seal. This continuous interruption of the stream of loose material from a starting sample which is to be delivered and divided up produces a markedly improved uniformity on the periphery of the divider cone than is possible with a sleeve valve which opens only once and remains open.

THE DRAWINGS

The invention will be explained in greater detail below with the aid of one embodiment which is illustrated in the drawings. In the drawings.

DETAILED DESCRIPTION

Figure 1:
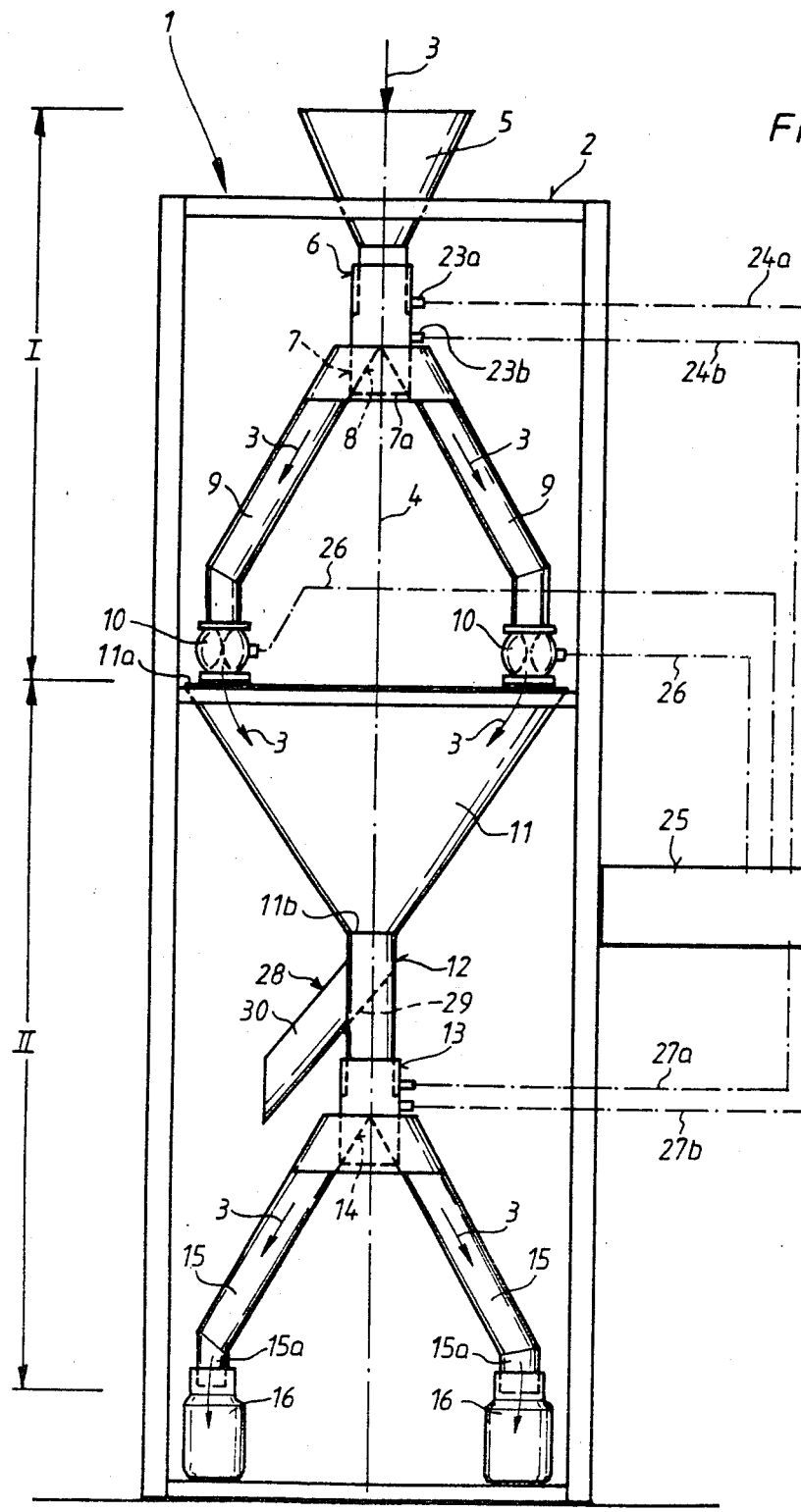
FIG. 1 shows a largely schematic overall view of a sample divider.

The general construction of a preferred embodiment of the sample divider 1 will be explained with the aid of the largely schematic FIG. 1. This sample divider 1 can be arranged and retained in a suitable frame 2. The direction of flow of a starting sample of fine-grained loose material which is to be divided up is indicated by the arrows 3 in FIG. 1. If one considers the overall construction of the sample divider 1 as illustrated in FIG. 1, then the following parts are arranged below one another in this flow direction (arrow 3) and symmetrically with respect to a common vertical axis 4: a sample delivery funnel 5 of symmetrical construction to receive the starting sample, a sample delivery pipe 6 connected directly to the lower end thereof and having a first sliding sleeve 7 constructed on its lower end, a first divider cone 8 provided below the opening end 7a of the first sliding sleeve 7, a plurality of first sub-sample pipes 9 coming out of the said divider cone 8, inclined downwards and directed outwards and having closable valves 10 at their lower ends, a symmetrical straight collecting funnel 11 tapering downwards with a discharge pipe 12 and a second sliding sleeve 13 arranged on its lower end, also a second divider cone 14, a plurality of second sub-sample pipes 15 coming out of the latter and inclined downwards and outwards, and a plurality of collecting vessels 16 which can be jars, metal boxes, bags or the like and are each releasably collected to the lower end 15a of one of the second sub-sample pipes 15.

In this construction and arrangement of the sample divider 1 the parts from the sample delivery funnel 5 to the valves 10 at the lower ends of the first sub-sample pipes for a first division stage I and the parts from the collecting funnel 11 to the second sub-sample pipes 15 or the collecting vessels 16 form a second division stage II.

The two divider cones 8 and 14 and the pipes 6 and 12 respectively arranged above them as well as the appertaining sliding sleeves 7 and 13 respectively constitute essential components of this sample divider 1. Since these arrangements in the region of each divider cone are of essentially the same construction, only the upper, first divider cone 8 with the components of the sample divider arranged before and after it will be explained with the aid of FIGS. 2 and 3.

The sample divider 8 is arranged centrally in a housing 17 which encloses it with radial spacing and into which the sliding sleeve 7 protrudes centrally from above, the said sliding sleeve 7 being constructed and retained so as to be movable in the direction of the double arrow 7b that is to say in a vertical direction at the lower end 6a of the sample delivery pipe 6 (which will be explained in greater detail below).

Figure 3:
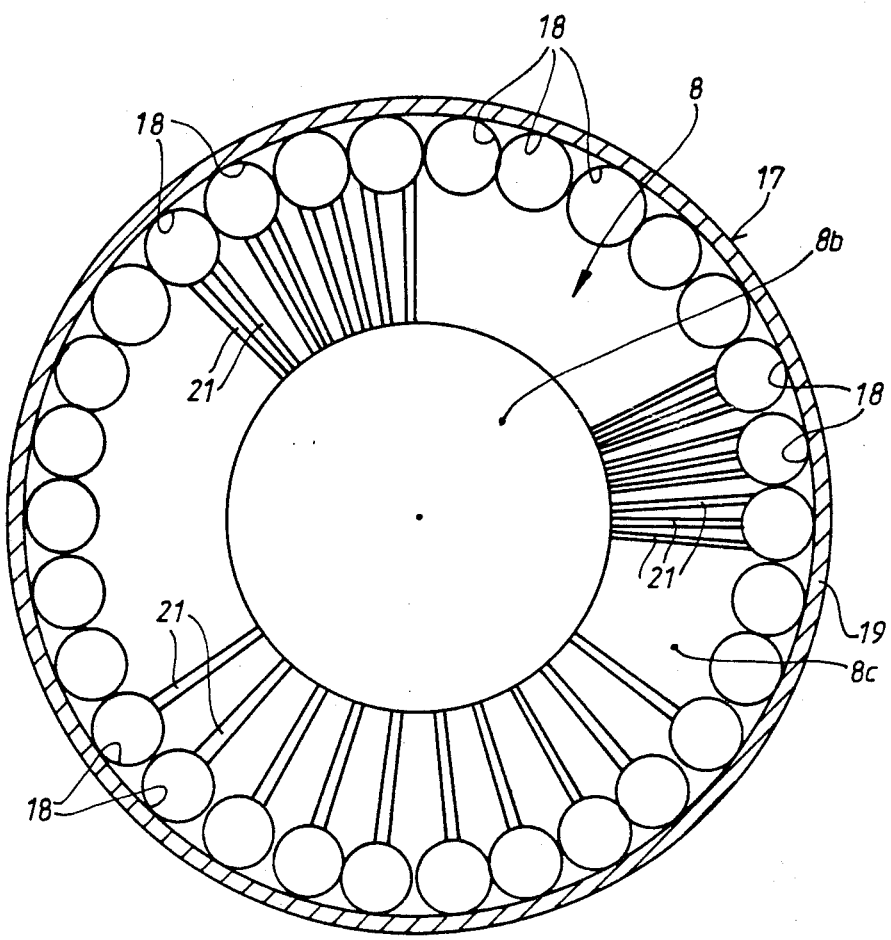
FIG. 3 shows a sectional view approximately along the line III—III in FIG. 2.

The divider cone 8 is constructed in a geometrically straight form with its apex pointing upwards, and a plurality of sample distribution holes 18 are provided in even distribution over the periphery of its (lower) base surface 8a; these sample distribution holes 18 are constructed in close succession in the annular space between the casing 19 of the housing 17 and the base surface 8a of the cone (cf. FIG. 3).

In a preferred embodiment each divider cone 8 or 14 is produced integrally with its housing 17 and the sample distribution holes 18 are constructed as bores.

It can also be seen in FIG. 2 that the upper ends of the first sub-sample pipes 9 are connected directly below the sample distribution holes 18, for example with suitable short pieces of pipe 20 interposed.

In the illustrated embodiment each divider cone 8 (or 14) has a smooth surface on its upper end 8b which cooperates with the lower opening end 7a of the sliding sleeve 7. By contrast the surface in the region of the lower half of the cone 8c is provided with continuous guide grooves 21 which are distributed evenly over the periphery and in plan view (FIG. 3) extend substantially radially. These guide grooves 21 can be adapted in their number and arrangement to the individual sample distribtuion holes 18 and in their cross-section to the grain sizes or the predominantly occurring grain sizes of the loose material to be divided up. At least one guide groove 21 runs to each sample distribution hole 18. Several possible constructions are indicated in FIG. 3. In the diagrammatic representation of FIG. 3, in the lower half one single guide groove 21 leads symmetrically (centrally) to each sample distribution hole 18; the left-hand upper quarter of the diagrammatic representation of FIG. 3 a possibility in which two guide grooves 21 can run to each sample distribution hole 18; and in the right-hand upper quarter in FIG. 3 three such guide grooves 21 run symmetrically to each sample distribution hole 18.

Figure 2:
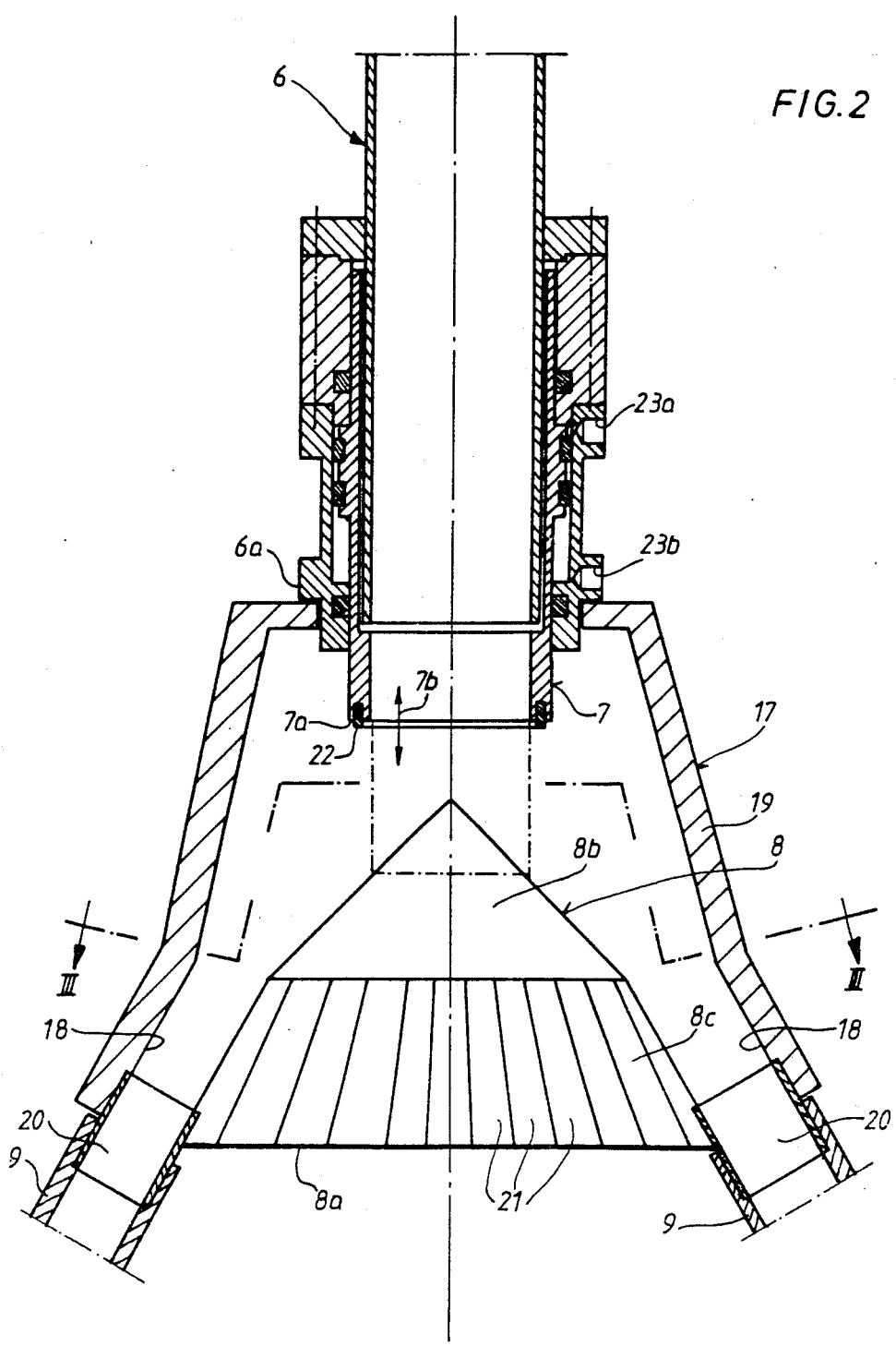
FIG. 2 shows a vertical sectional view in the region of a divider cone with a sliding sleeve arranged above it.

According to the representation in FIG. 2, the lower end 6a of the sample delivery pipe 6 is connected like a flange to the upper end of the housing 17 so that the sample delivery pipe 6 is stationary. The first sliding sleeve 7 is received inside the lower end 6a of the sample delivery pipe so as to be movable in a vertical direction (double arrow 7b) in such a way that its lower opening end 7a is movable in a pulsing fashion against the smooth surface of the upper end 8b of the divider cone and forms a seal. This lower opening end 7a therefore has a sealing ring 22 which projects downwards.

The sliding sleeve 7 with its lower opening end 7a can be driven pneumatically in order to enable it to move up and down in a pulsing fashion according to a chosen rhythm, and for this purpose it co-ooperates with the appertaining fixed pipe section located above it, that is to say in this case the lower end 6a of the delivery pipe 6, in the manner of a cylinder-piston arrangement. For this purpose compressed air connections 23a, 23b which are connected via suitable compressed air control lines 24a and 24b to a suitable compressed air source 25 are provided in the lower end 7a of the sample delivery pipe in which the sliding sleeve 7 is slidably received. Each compressed air connection 23a and 23b is connected to an appertaining sealed chamber constructed between the pipe end 6a and the sliding sleeve 7 in such a way than when the action of the compressed air changes the sliding sleeve 7 can be moved alternately upwards and downwards (as far as the surface of the divider cone 8). Adjustable control arrangements which are suitable for this purpose are generally known and do not therefore need to be explained in detail.

As has already been mentioned above, the lower second divider cone 14 and the appertaining second sliding sleeve 13 are constructed from a design point of view in the same way as the upper first divider cone 8 with its appertaining components. The same number of sample distribution holes 18 or a different number, for example a smaller number, of sample distribution holes can be provided around the base surface of the lower second divider cone 14; this can be adapted to the particular circumstances of use in the sample divider. According to the representation in FIG. 3 it may be assumed that thirty sample distribution holes are provided in close succession in the peripheral direction, at least on the upper first cone 8.

For the valves 10 arranged at the lower ends of the upper first sub-sample pipes 9 any suitable type of valve can generally be used. Presser valves 10 which can be actuated pneumatically and as required are regarded as particularly advantageous. These pneumatic presser valves 10 can be standard presser valves, so that it is not necessary to describe them in detail. These presser valves 10 are preferably also connected via compressed air control lines 26 to the compressed air control source 25 to which the lower second sliding sleeve 13 is als connected via separate compressed air control lines 27a and 27b.

The pneumatic presser valves 10 are arranged in even distribution on the upper peripheral edge 11a of the collecting funnel 11 which tapers conically downwards. This collecting funnel 11 can be a funnel of quite simple construction without any internal components. The discharge pipe 12, the lower end of which-as described-described is constructed with the second sliding sleeve 13, is directly connected to the lower outlet end 11b of the collecting funnel 11.

A branch pipe 28 is preferably also built into the discharge pipe 12 above the second sliding sleeve 13 and contains as essential parts a deflector 29 which can be pivoted into the pipe cross-section of the discharge pipe 12 and an outer outlet pipe 30 to draw off (discard) proportions of samples which are not required.

This sample divider is particularly suitable for fine-grained loose material with a grain size of equal to or less than approximately 5 mm. It can be used both in research laboratories of establishments which process loose material and in the appropriate sections of organisations in which the samples to be studied are taken.

One embodiment of this sample divider will be described below in which it is assumed that in the first division stage I the first divider cone 8 is constructed with thirty sample distribution holes 18 and thirty first subsample pipes 9 connected thereto, and in the second division stage II the second divider cone 14 is constructed with twenty-four sample distribution holes and twenty-four second sub-sample pipes 15 connected thereto. It should also be assumed that fine coal with a grain size of at most 3 mm is to be studied and the starting sample is approximately 3000 g, from which two samples each of 100 g and two samples each of 500 g are to be divided, whilst the remaining quantity, that is to say the proportion of the sample amounting to over 1200 g, is to be discarded.

The starting sample (3000 g) is put into the sample delivery funnel 5. In the static sample division now occurring (division only with free-flowing loose material) the sample quantity in the first division stage passes via the sample delivery pipe 6 and the first sliding sleeve 7 which is movable upwards and downwards in a pulsing fashion to the first divider cone 8, where a first even division of the starting sample takes place to the thirty sample distribution holes and the thirty first sub-sample pipes 9 connected thereto which are all closed at the bottom by their presser valves 10. As a result of this first division of the starting sample each first sub-sample pipe 9 contains a substantially equal quantity, i.e. with thirty sub-sample pipes 9 each of these pipes contains a sub-sample quantity of approximately 100 g. In order now-as assumed-to divide off two samples each of 100 g and two samples each of 500 g, a total of 1200 g of the starting sample quantity is let into the collecting funnel 11 for the second division stage II, and for this purpose the presser valves 10 of twelve selected first sub-sample pipes 9 are opened so that twelve times 100 g=1200 g of the starting sample quantity enter this collecting funnel. For this second division the loose material flows from above out of the collecting funnel 11 via the discharge pipe 12 and the second sliding sleeve 13 (which is moved up and down in a pulsing fashion like the first sliding sleeve 8) and centrally onto the second divider cone 14. In exactly the same way as the first divider cone 8, the second divider cone 14 now divides the 1200 g sample delivered to it into twenty-four sub-sample quantities of equal size and passes these sub-samples via the second sub-sample pipes 15 to the appropriate collecting vessels 16. Thus with the relatively uniform division of the starting sample quantity which can be achieved using this sample divider 1 each collecting vessel 16 contains a sub-quantity of 50 g. By the appropriate bringing together of the sub-quantities from the collecting vessels 16 it is then possible-as required in this case-to prepare two sub-samples each of 100 g and two sub-samples each of 500 g.

After the second division in the second division stage II is completed, the deflector 29 of the branch pipe 28 is pivoted completely into the cross-section of the discharge pipe 12 so that after all the presser valves 10 of the first sub-sample pipes 9 which are still closed have been opened the remaining losse material of the starting sample quantity can be drawn off via the outlet pipe 30 and discarded.

It should finally be stated that in the sample divider 1 which has been described the presser vavles 10 or valves of other construction can basically be controlled in any suitable way. However, the compressed air control of each pneumatic presser valve 10 as indicated produces not only a relatively simple central control but also the advantage that in particular in larger sample preparation installations the sample division can be designed in an extremely advantageous manner so as to be programmable. In this way for the second division stage the sub-samples contained in the first sub-sample pipes 9 can be drawn off from there in a pre-programmable and variable manner.

What is claimed is:

1. In a sample divider for fine-grained loose material samples having:
    a. a first substantially vertical sample delivery pipe;
    b. a divider below said delivery pipe, and
    c. a plurality of collecting vessels below the divider for receiving a sub-sample in each,
   the improvement comprising:
    d. a divider cone with its apex uppermost and positioned centrally below said delivery pipe, said cone having a base surface provided with a plurality of sample distribution holes distributed evenly over the periphery of said base surface;
    e. a slidable sleeve at the lower end of said delivery pipe and being vertically movable between said delivery pipe and said cone;
    f. means for pulsing said sleeve vertically between a lower position with its lower end in sealing engagement with the upper surface of said divider cone and an upper position spaced therefrom;
    g. a collecting funnel below said cone for receiving material from said holes, said funnel having an outlet at its lower end;
    h. pipe means, including a plurality of individually operable valves, for discharging material from said cone to said funnel; and
    i. means connecting said outlet of said connecting funnel to sample collecting vessels, said connecting means including a discharge pipe at the outlet end of said funnel, a second divider cone arranged below said discharge pipe with its upper surface in communication with said discharge pipe, and a plurality of sub-sample pipes each for delivering material from said second cone to a different one of said sample collecting vessels.

2. A sample divider as claimed in claim 1 wherein said second divider cone has the same configuration as said first divider cone, said collecting funnel having a second discharge pipe opening centrally above said second divider cone and including a second, vertically movable sleeve, the lower end of said second sleeve being thereby movable toward and from the surface of said second divider cone between a first position forming a seal therewith and a second position spaced therefrom.

3. A sample divider as claimed in claim 2, including a housing arranged centrally about each of said divider cones enclosing each of said cones with radial spacing therefrom, said sample distribution holes being included in close succession in the radial space between the casing of said housing and the base surface of said cone, said sliding sleeves in each instance projecting centrally from above into said housing.

4. A sample divider as claimed in claim 3, wherein each of said divider cones is integral with its respective housing, said sample distribution holes being constructed as bores in said housing.

5. A sample divider as claimed in claim 3, wherein each of said divider cones has a smooth surface at least on its upper end.

6. A sample divider as claimed in claim 5, wherein the surface of each of said divider cones includes approximately in the region of its lower half thereof continuous guide grooves extending essentially radially and evenly distributed over its periphery, at least one of said guide grooves running to each of said sample distribution holes.

7. A sample divider as claimed in claim 1, wherein said sleeves are of similar construction, each of said sleeves and the appertaining pipe associated therewith including surfaces forming a cooperating cylinder on one and piston on the other, and including pneumatic means for effecting pulsing movements of said sleeves.

8. A sample divider as claimed in claim 1, wherein said valves are located at the lower ends of said pipe means, each of said valves including means for pneumatic actuation.

9. A sample divider as claimed in claim 8, comprising means mounting said valves in even distribution over the upper peripheral edge of said collecting funnel, said funnel extending conically downward from said peripheral edge.

10. A sample divider as claimed in claim 1, including a branch pipe extending from said discharge pipe of said collecting funnel to a point above said second sleeve, said branch pipe being effective to draw off proportions of samples which are not required.

11. A sample divider as claimed in claim 1, including a symmetrically constructed sample delivery funnel, and means connecting the upper end of said sample delivery pipe to the lower end of said delivery funnel.

* * * * *